United States Patent [19]

Patton et al.

[11] Patent Number: 4,836,201
[45] Date of Patent: Jun. 6, 1989

[54] "ENVELOPE" APPARATUS FOR INSERTING INTRA-OCULAR LENS INTO THE EYE

[75] Inventors: Douglas M. Patton, Irvine; Matthew F. Duncan, Mission Viejo, both of Calif.

[73] Assignee: Patton Medical Technologies, Inc., Costa Mesa, Calif.

[21] Appl. No.: 172,371

[22] Filed: Mar. 24, 1988

[51] Int. Cl.⁴ .............................................. A61B 17/00
[52] U.S. Cl. ...................................... 128/303 R; 623/6
[58] Field of Search ......................... 128/303 R; 623/6

[56] References Cited

U.S. PATENT DOCUMENTS

| | | | |
|---|---|---|---|
| 4,681,102 | 7/1987 | Bartell | 128/303 R |
| 4,702,244 | 10/1987 | Mazzocco | 128/303 R |
| 4,715,373 | 12/1987 | Mazzocco | 128/303 R |

Primary Examiner—Michael H. Thaler
Attorney, Agent, or Firm—Lyon & Lyon

[57] ABSTRACT

There is disclosed herein an apparatus and method for curling and confining a flexible lens and for inserting and injecting the lens into the eye. The apparatus includes an insertion cartridge including a delivery envelope having a lens holder essentially in the form of an envelope or like a flower petal, a constricting sheath which is slid relative to the envelope to cause the envelope to curl within the tip of the sheath and thereby curl and confine a lens disposed in the envelope, and a reentry barrier operating in conjunction with both the envelope and the sheath for facilitaing injection and delivery of the lens into the eye and for enabling retraction of the envelope into the sheath. The tip of the envelope is configured somewhat like a flower petal to enable the lens to be curled as the sheath is moved over the envelope, and to allow the delivery envelope to "flower out" and the lens uncurl as the envelope is pushed from the sheath. There also is disclosed an hand held pen to which the insertion cartridge is attached for manipulation during the surgical procedure, and a control unit and control system for controlling advancement of the lens out of the lens cartridge as well as retraction of the envelope. Also disclosed is a lens cartridge loader and package for the lens cartridge and lens.

7 Claims, 9 Drawing Sheets

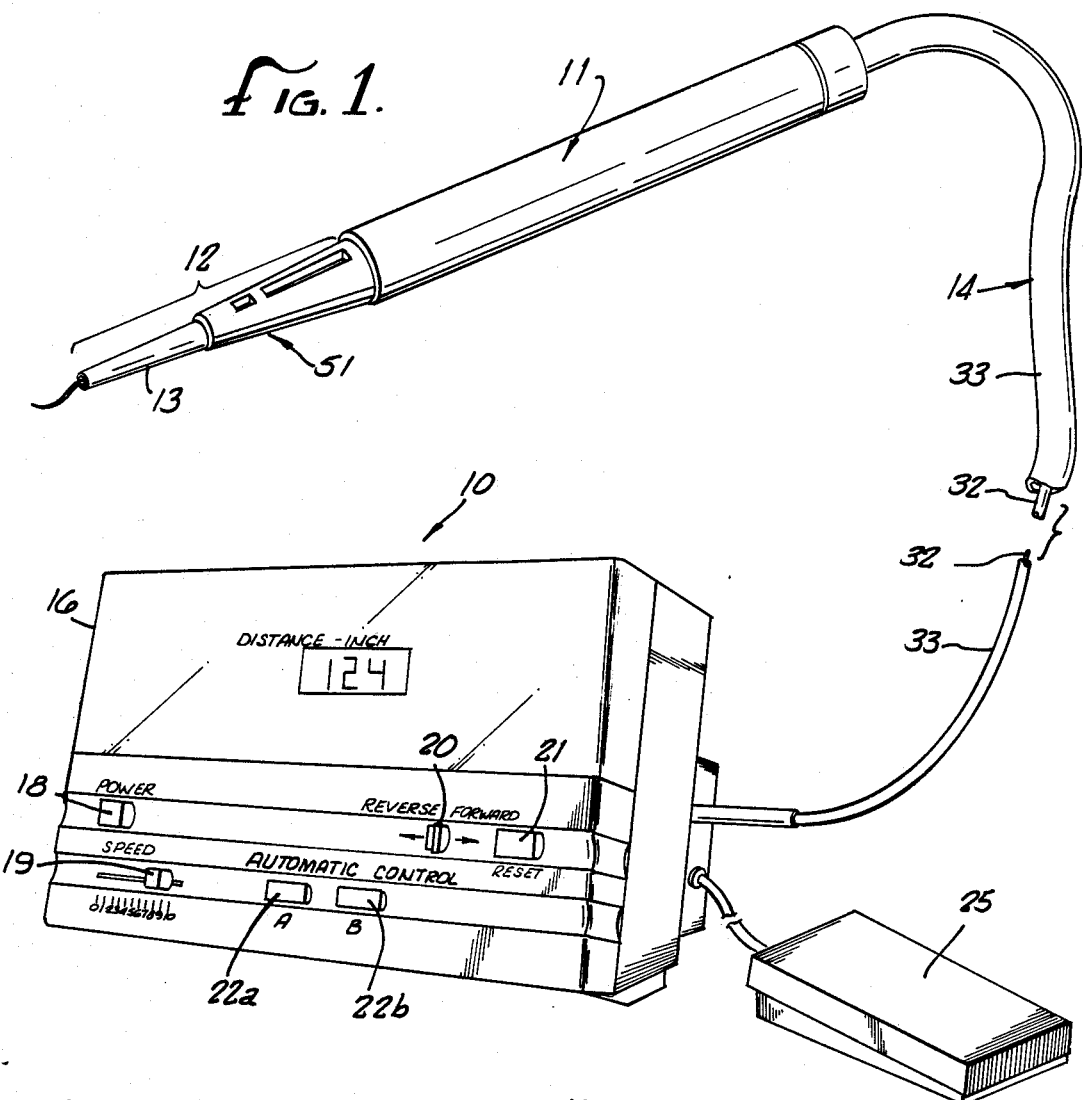
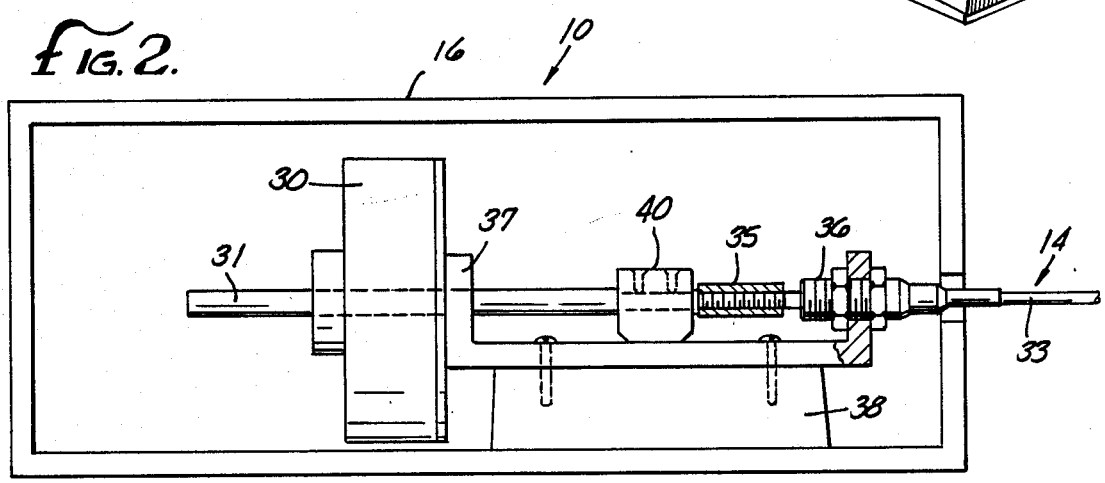

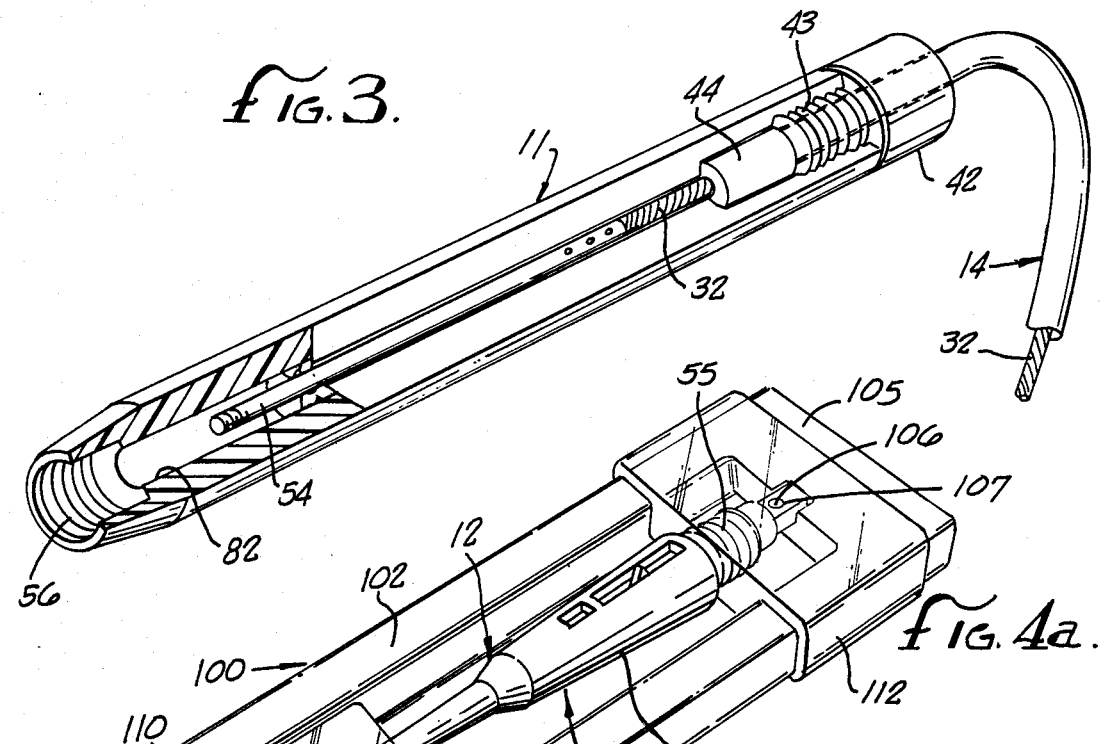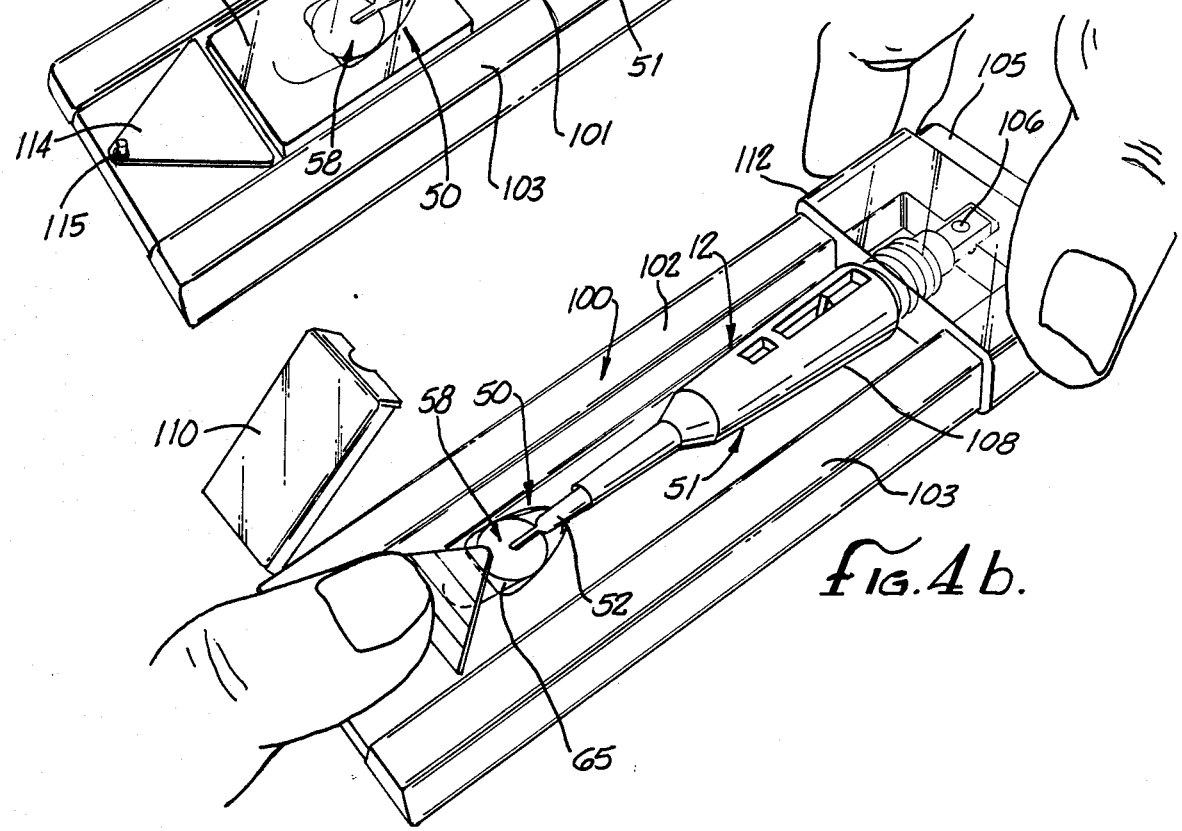

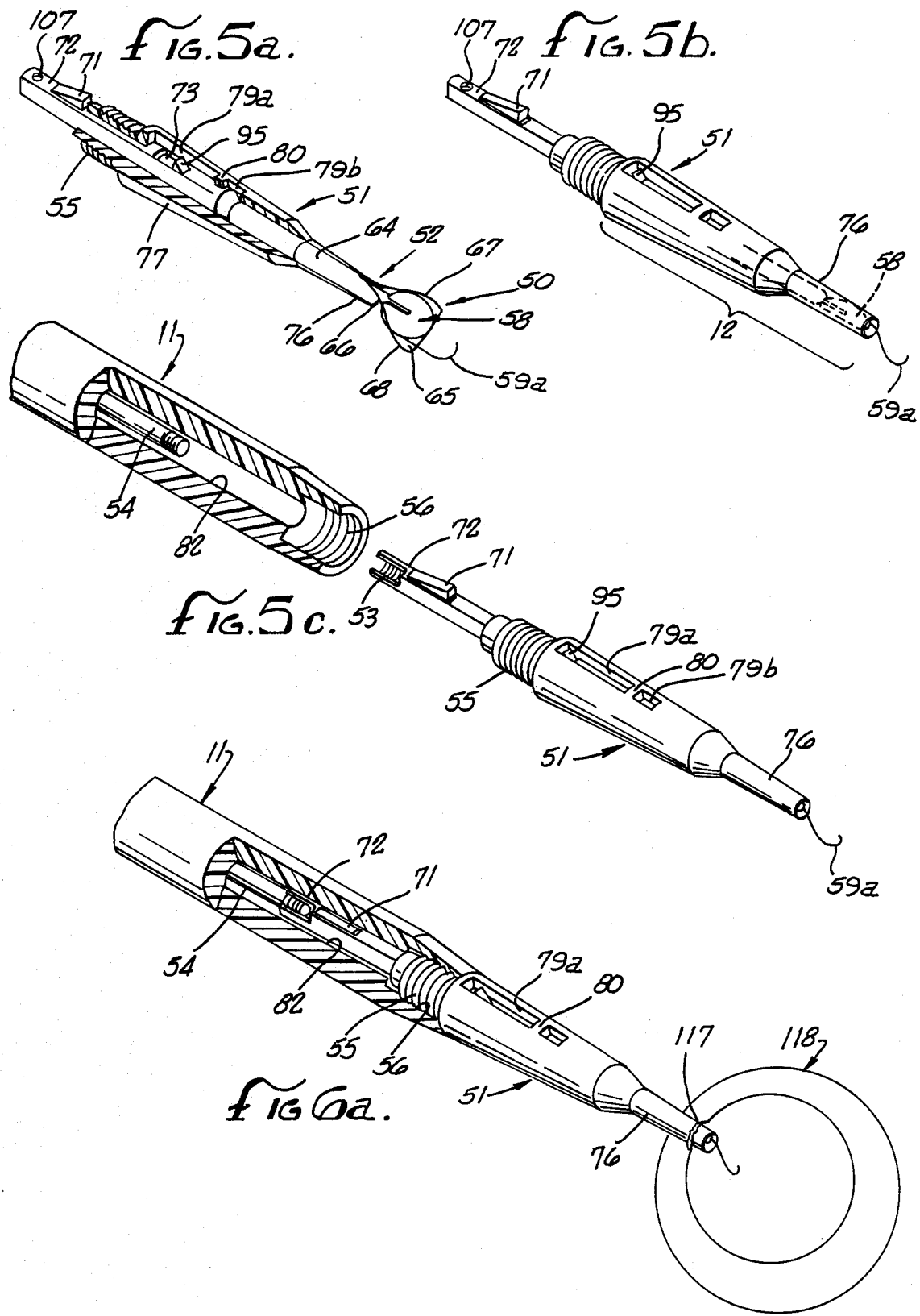

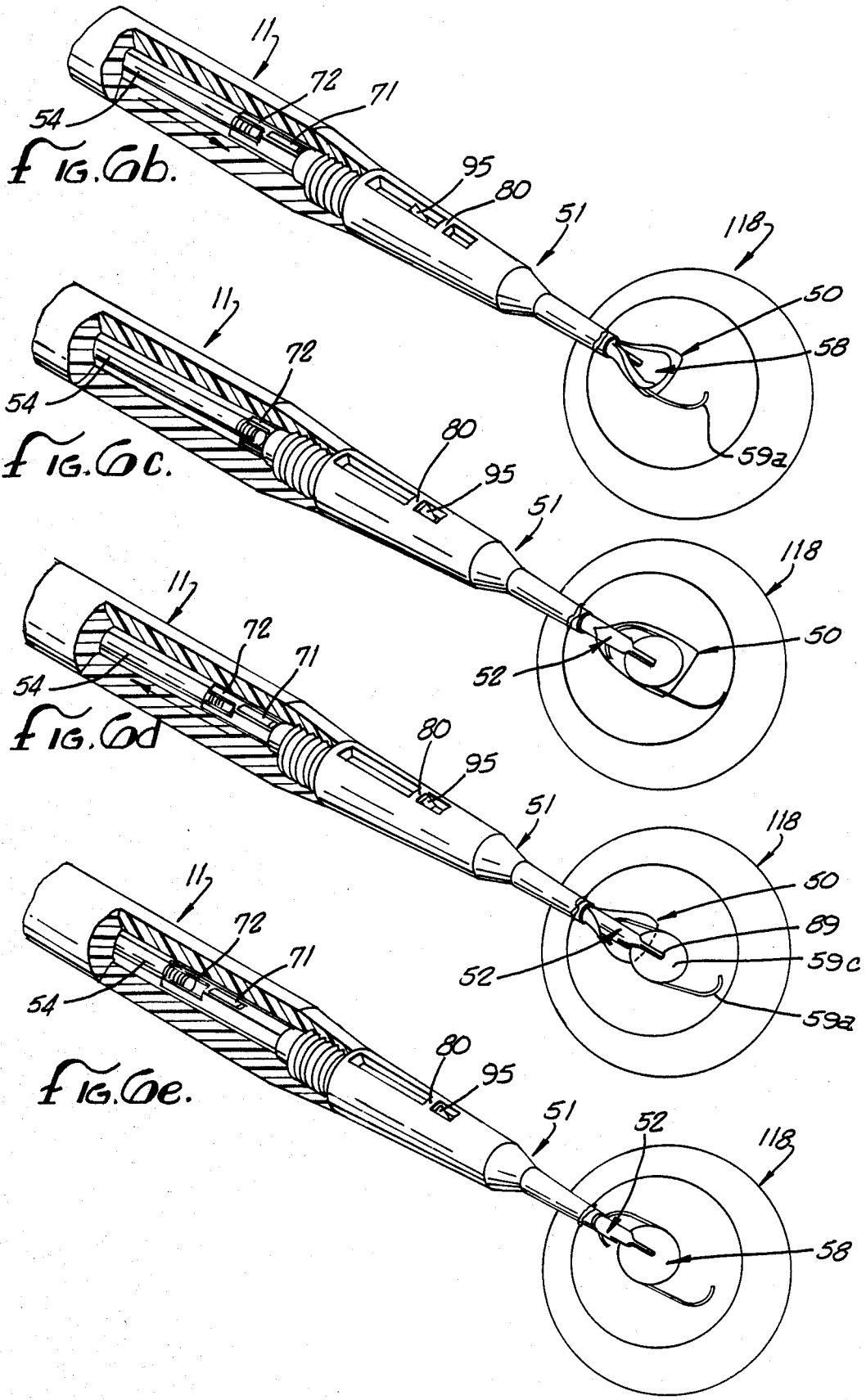

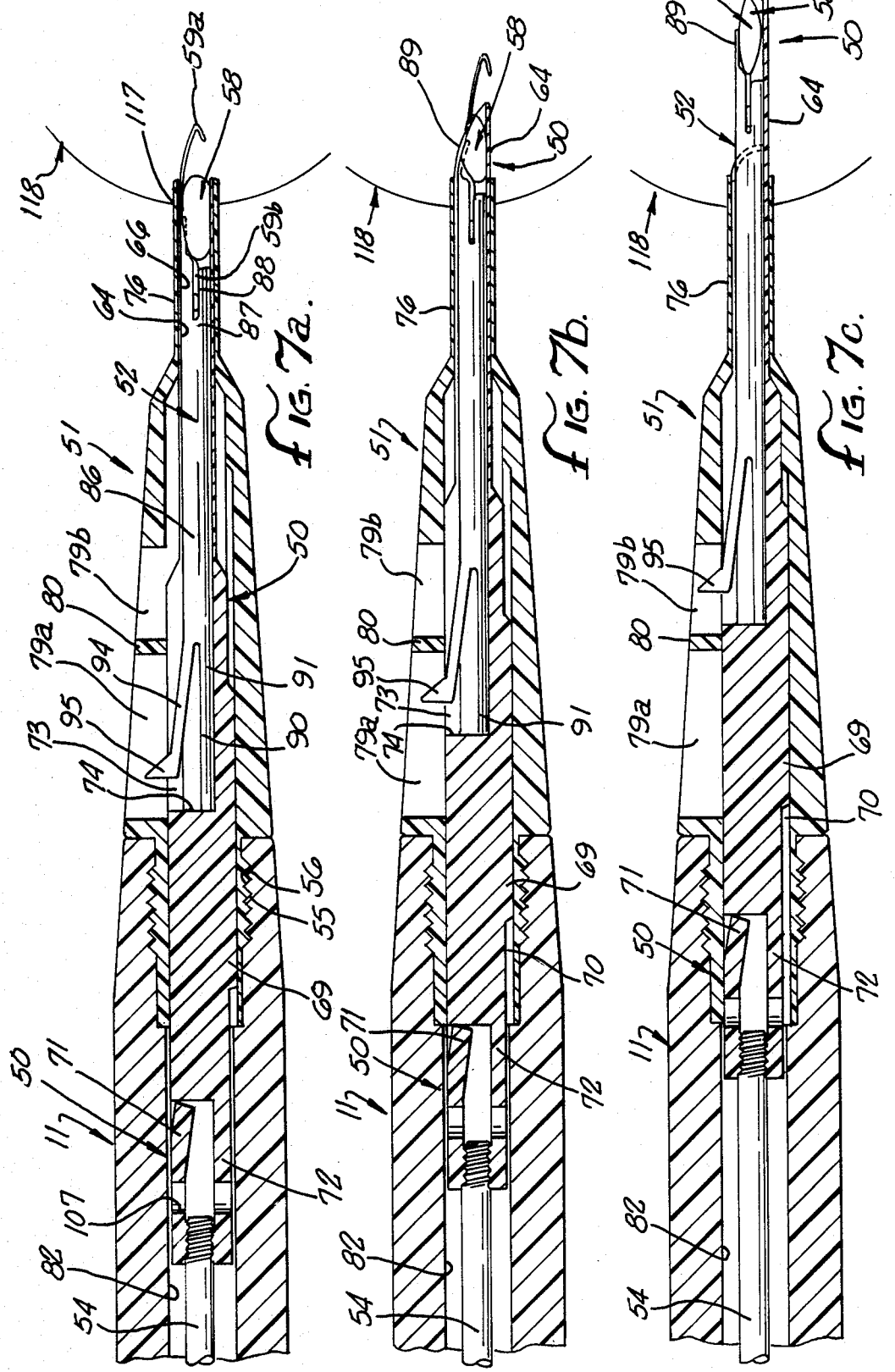

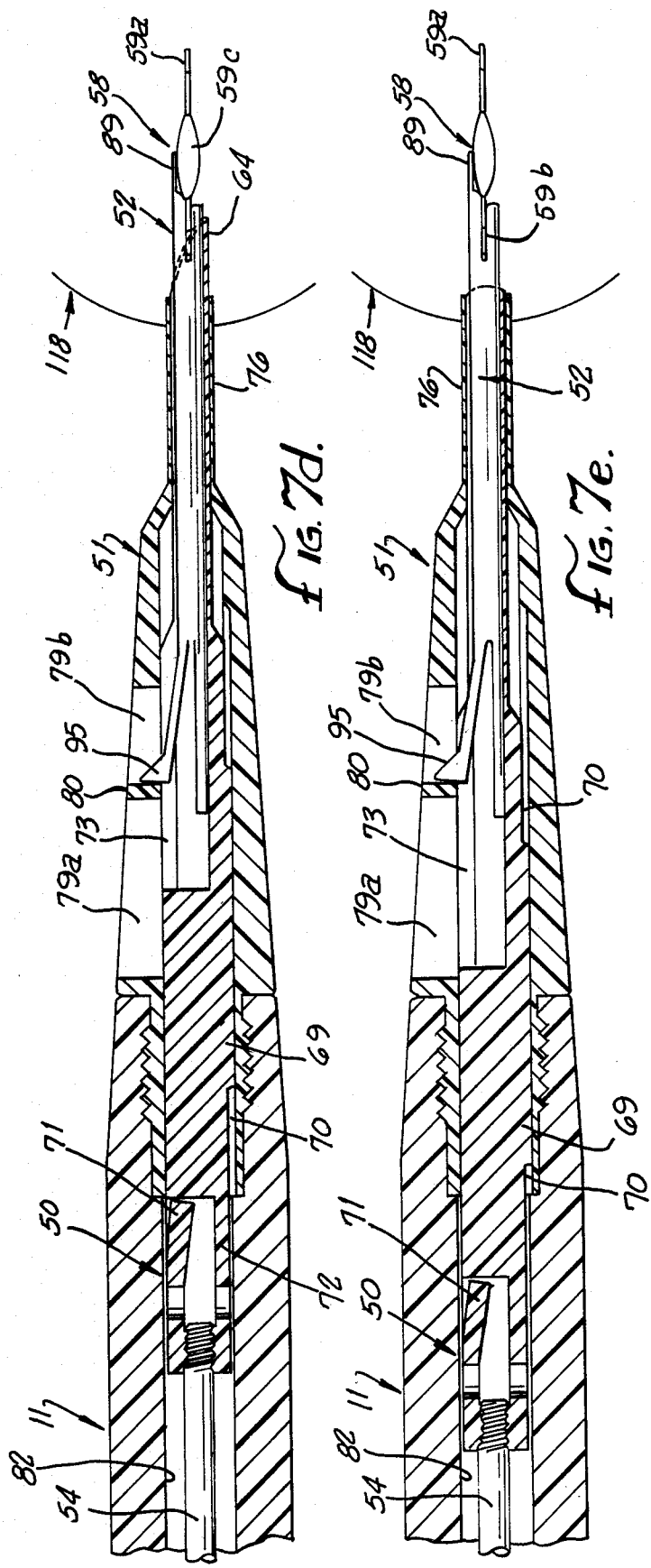

"ENVELOPE" APPARATUS FOR INSERTING INTRA-OCULAR LENS INTO THE EYE

CROSS-REFERENCE TO RELATED APPLICATIONS

The present application is related in subject matter to U.S. patent application Ser. No. 07/106,044 filed Oct. 7, 1987 entitled "APPARATUS FOR INSERTING ARTIFICIAL INTRA-OCULAR LENSES INTO HUMAN EYES FOR LENS IMPLANTING," and Ser. No. 172,374 filed concurrently herewith in the names of the present inventors entitled "CANOE APPARATUS AND METHOD FOR INSERTING INTRA-OCULAR LENS INTO THE EYE", both applications being assigned to the assignee of the present invention. The disclosures of the above applications are incorporated herein by reference.

BACKGROUND OF THE INVENTION

1. Field of the Invention

The present invention relates generally to the field of apparatus and methods for surgically implanting artificial lenses in the human eye, and particularly to the implanting of artificial intra-ocular lenses in cataract surgery in place of diseased or damaged natural intra-ocular lenses as part of the lens implanting operation.

2. Discussion of the Background

Vision is the ability of the eye to form an image of an object and send the image to visual centers of the brain. In this process, light rays from the object pass through the cornea, the aqueous humor, the pupil, the intra-ocular lens (IOL) and the vitreous humor of the eye. These rays finally reach the retina where they stimulate the optic nerve cells. In turn, the optic nerve carries "messages" from the nerve cells to the visual cortex of the brain. The disc-shaped intra-ocular lens in the eye performs the same function as the lens of a camera and is responsible for focusing incoming light rays onto the retina, which is the image registering portion of the eye.

Injury and disease can affect the ability of an intraocular lens to perform its function of focusing and transmitting light rays. In particular, a cataract is a lessening of the transparency of the lens when the normally clear fibers, which comprise the lens, become cloudy. As a consequence, adequate light cannot reach the associated retina, and vision becomes increasingly blurred. Cataracts tend to be relatively common in persons over about 65 or 70 years of age; however, in younger persons a cataract may be present at birth or may result at any age from injury or disease. Diabetes can, for instance, cause cataracts to occur, as can glaucoma.

So far, as is known, there presently exists no treatments or medicines which can reverse a cataract and cause the cloudy lens fibers to become clear and transparent again. The only effective treatment for a cataract is surgical removal of the affected lens, and, until relatively recently, optical compensation for a removed lens was limited to strong glasses which were clumsy and heavy or contact lenses, although the latter are frequently incapable of providing sufficient focusing effect.

Medical technology has, however, recently advanced to the state that a diseased or damaged intra-ocular lens can now be replaced by an artificial intra-ocular lens which is surgically implanted in the eye behind the cornea after the natural lens has been removed. These artificial lenses can, like regular glasses or contact lenses, be specially made to correct other eye deficiencies and are, for example, commonly available in a variety of diopters. A typical medical protocol followed in replacing a diseased or damaged, natural intra-ocular lens with an artificial intra-ocular lens involves first making a small surgical incision or aperture in the cornea near its edge and to one side of the iris. The diseased or damaged natural intraocular lens is surgically removed through this corneal aperture, by such means as ultrasonically fracturing the lens and then extracting, as by the application of suction, the lens tissue. Next, an artificial replacement lens is carefully inserted into the eye through the same corneal aperture and is manipulated by the surgeon into the same position, behind the iris, previously occupied by the removed natural lens. According to the particular configuration of the artificial lens being installed, appropriate surgical techniques are then used to secure the artificial lens in its proper position in the eye. Finally, the incision made through the cornea is repaired.

For this type of surgical lens implantation procedure, it is known to use a flexible artificial lens, constructed of a material such as silicone, and to manually bend or curl the lens, for example, by forceps, into a tubular shape before insertion so that the size of the corneal aperture needed for insertion can be made as small as possible to minimize trauma to the eye. As soon as the artificial lens, when curled into tubular form, is inserted through the corneal aperture and is released, it uncoils on its own into its original flat, disc shape. This procedure of coiling an artificial lens into tubular form permits, by way of illustration, an artificial lens having a diameter of about one quarter inch to be inserted through a corneal opening only about one tenth of an inch across. The use of the above-described type of intra-ocular lens implantation technique is disclosed, for example, in U.S. Pat. No. 4,573,998 to T. Mazzocco, the disclosure of which is incorporated herein by reference.

Small artificial intra-ocular lenses are, however, extremely difficult to manually fold or curl into a small shape by forceps or other conventional medical instruments without scratching or otherwise damaging the lens. Moreover, the eye itself is so extremely delicate that even the merest touch of the tip of a surgical instrument or of an edge of the artificial lens on the one-cell layer of the endothelial lining on the posterior face of the cornea can tear some of the cells away from the corneal surface and permanently injure the eye.

Because of the difficulty in manually curling and inserting an artificial lens through a small incision in the cornea, various lens inserting instruments or apparatus have been developed or proposed for mechanically folding a flexible artificial lens and for then inserting the lens through the corneal incision into the eye. One such type of artificial lens inserting instrument believed to have been used in surgical lens implanting resembles a hypodermic syringe, in that it has a cylindrical barrel with an internal plunger and a converging, funnel-shaped insertion tip and a flanged chamber for holding the lens. A device of this nature is disclosed in U.S. Pat. No. 4,681,102.

In using such a syringe-type instrument, an artificial intra-ocular lens to be implanted in a patient's eye is placed in the instrument barrel and folded therein. An appropriate surgical incision is made in the patient's cornea and the natural intra-ocular lens is removed in a manner such as described above. The end of the insertion tip is then inserted through the corneal incision and the plunger of the instrument is depressed so as to push against a side edge of the artificial lens in the barrel. Depressing the plunger of the instrument forces the lens out of a cylindrical tip of the instrument and into the patient's eye.

A principal disadvantage associated with such types of artificial lens inserting instruments is that the lens tends to abruptly spring out of the tip. As has been emphasized above, an eye is extremely delicate and any abrupt ejection of the replacement lens from the inserting instrument into a patient's eye can result in the lens damaging delicate eye tissue and causing eye injury.

Even if the lens itself does not cause any eye injury in such circumstances, the abrupt ejection may result in the lens being incorrectly positioned in the eye, and the additional manipulation required to correctly position and align the lens may injure the eye. Further in this regard, it is also highly desirable that the lens transplant operation be completed as rapidly as possible and the corneal incision be quickly repaired so as to minimize trauma to the eye and reduce the possibility of infection. Therefore, the lens insertion instrument used should accurately position the artificial lens as the lens is inserted into the eye, so that the amount of subsequent manipulation of the lens is kept to a minimum.

For these and other reasons related to minimizing trauma to a patient's eye during and as a result of any intraocular lens transplant operation, improvements are needed to lens inserting apparatus and methods. Ideally, such improved apparatus should provide the ophthalmic surgeon who performs lens transplant operations complete and precise control of lens insertion into the patient's eye and should, therefore, eliminate or at least substantially reduce any tendency of the replacement lens to abruptly spring out of the insertion instrument into the eye during the insertion process. Additionally, such improved apparatus should leave at least one of the performing surgeon's hands free to hold other instruments, manipulate the patient's eye or otherwise assist with the operation.

The inventions described in applicants' previously referenced U.S. Patent applications provide significant improvements in these respects. The apparatus and method disclosed in application Ser. No. 07/106,044 provides a convenient and simple means of receiving, holding and confining an intra-ocular lens, and one which provides an injector tip configuration and controlled movement of the lens out of the instrument in a manner to reduce abrupt springing of the lens out of the tip. The invention of the application referred to above and which is filed concurrently herewith shows and describes an improvement and modification of the apparatus and method disclosed in U.S. patent application Ser. No. 07/106,044 in that it provides improved lens holder and injector tip configurations, and means and methods of more gently passing the lens out of the tip and into the eye. The present application shows and describes an entirely different technique wherein the lens is held and curled in what may be termed an "envelope" fashion and in which the lens as it moves out of the tip gently "flowers out" to further minimize problems with prior approaches.

SUMMARY OF THE INVENTION

The present invention provides a medical apparatus and method for inserting a flexible artificial intra-ocular lens into a patient's eye through a small incision therein for the replacement of a removed natural lens. While the present apparatus and method will be described specifically with respect to insertion of an intra-ocular lens, the apparatus and method of the present invention also are applicable in refractive surgery in the cornea of the eye.

The apparatus of the present invention includes three major components, namely a control unit, hand held instrument and lens insertion cartridge. The hand held instrument preferably is connected at one end to the control unit by a flexible drive cable, and the insertion cartridge is attached to the other end of the instrument. The instrument provides a convenient means whereby the physician can hold and operate the insertion cartridge with one hand, and the instrument is connected to the control unit by the flexible drive cable which provides a controlled force to advance the lens through and out of the cartridge and into the eye during the surgical procedure. The instrument and control unit, while not identical, are similar to those shown and described in said above referred to applications.

The insertion cartridge comprises three major components. One is a constricting sheath which is attached to the hand held instrument or pen at one end and which has a tiny cylindrical distal tip portion for insertion into the eye. The second component is an elongated delivery envelope which has a thin distal end which normally is open and "flowered out" for receiving a lens, and which may be retracted into the sheath for curling the lens in the distal end of the envelope and within the cylindrical distal end of the sheath. The delivery envelope includes a proximal tubular end which is connected with a drive shaft of the pen for causing the delivery envelope to extend out of the distal end of the sheath and to retract back into the sheath during delivery of the lens into the eye. The third component is a re-entry barrier which is disposed within the delivery envelope, and which has a distal end which preferably is slotted for engaging the lens and a proximal end which enables the barrier to be moved in one direction with the envelope and which performs a locking function in conjunction with the sheath in another direction. This barrier and its slotted distal end assists in holding and stabilizing the lens in the eye as the delivery envelope is retracted into the sheath.

The delivery envelope has a distal end essentially in the shape of a tube but which is slit from the end a short distance so that the distal end normally is in what may be termed a "flowered open" state (somewhat like an open flower petal) in which it receives the intra-ocular lens and in which state it serves to deliver the intra-ocular lens. The shape and construction of particularly the distal end of the delivery envelope along with the manner in which it is moved with respect to the sheath and in conjunction with the re-entry barrier, and along with the controlled advancement and retraction of the delivery envelope by a drive shaft in the pen as controlled by the control unit, allow the IOL to be injected into the eye and to progressively and gently return to its original shape as it is moved out of the tip of the sheath because of the gentle "flowering out" action provided by the delivery envelope as the envelope moves out of the sheath.

Accordingly it is a principal object of the present invention to provide an improved form of apparatus and method for inserting artificial lenses.

Another object of this invention is to provide an improved form of apparatus and method for inserting artificial intra-ocular lenses into human eyes.

A further object of the present invention is to provide a new form of lens insertion cartridge for facilitating gentle insertion of an intra-ocular lens into the eye.

Another object is to provide a lens insertion cartridge wherein the structure and configuration of the components thereof and the drive means therefor, enable the lens to be gently inserted into the eye.

Another object of the present invention is to provide a new form of artificial lens insertion device comprising a delivery envelope and associated sheath for enabling simple and efficient curling of the lens into the envelope and for facilitating gentle and controlled movement of the thus-curled lens out of the envelope and into the eye.

A further object of the present invention is to provide a new form of artificial lens insertion device incorporating a delivery envelope having a slotted distal end, used in conjunction with a constricting sheath and re-entry barrier, and wherein the delivery envelope serves to curl a lens placed therein when the envelope is retracted into the sheath and wherein the envelope upon movement from the sheath allows gentle "flowering out" of the lens into the eye.

A further object of the present invention is to provide an intra-ocular lens cartridge loader.

BRIEF DESCRIPTION OF THE DRAWINGS

These and other objects and features of the present invention will become better understood through a consideration of the description herein taken in conjunction with the drawings in which:

FIG. 1 is a perspective view of a control unit, hand held instrument, and lens insertion cartridge according to the present invention;

FIG. 2 is an elevational cross-sectional view of a stepper motor drive used in the control unit and for pushing an intra-ocular lens from the insertion cartridge into the eye;

FIG. 3 is a cross-sectional view of the hand held instrument or pen with the flexible drive cable from the control unit attached at the proximal (right in the Figure) end thereof;

FIGS. 4a and 4b illustrate a loading mechanism for holding the lens insertion cartridge and for facilitating simple loading of a lens into the cartridge and which mechanism may serve as a sterile package for the lens and cartridge;

FIGS. 5a, 5b and 5c respectively illustrate the lens disposed in a delivery envelope ready to be retracted into a constricting sheath (FIG. 5a), the cartridge loaded with the curled lens (FIG. 5b), and the thus-loaded cartridge ready for attachment to the distal end of the pen;

FIGS. 6a through 6e are partial cross-sectional perspective views of the insertion cartridge and the distal end of the pen, and illustrate the tip of the cartridge inserted into an incision in the eye, and particularly illustrate the injection process of the lens into the eye from the apparatus;

FIGS. 7a through 7e are detailed cross-sectional views of the insertion cartridge and distal end of the pen during the lens ejection sequence as respectively illustrated in FIGS. 6a through 6e;

DETAILED DESCRIPTION

Figure 8:
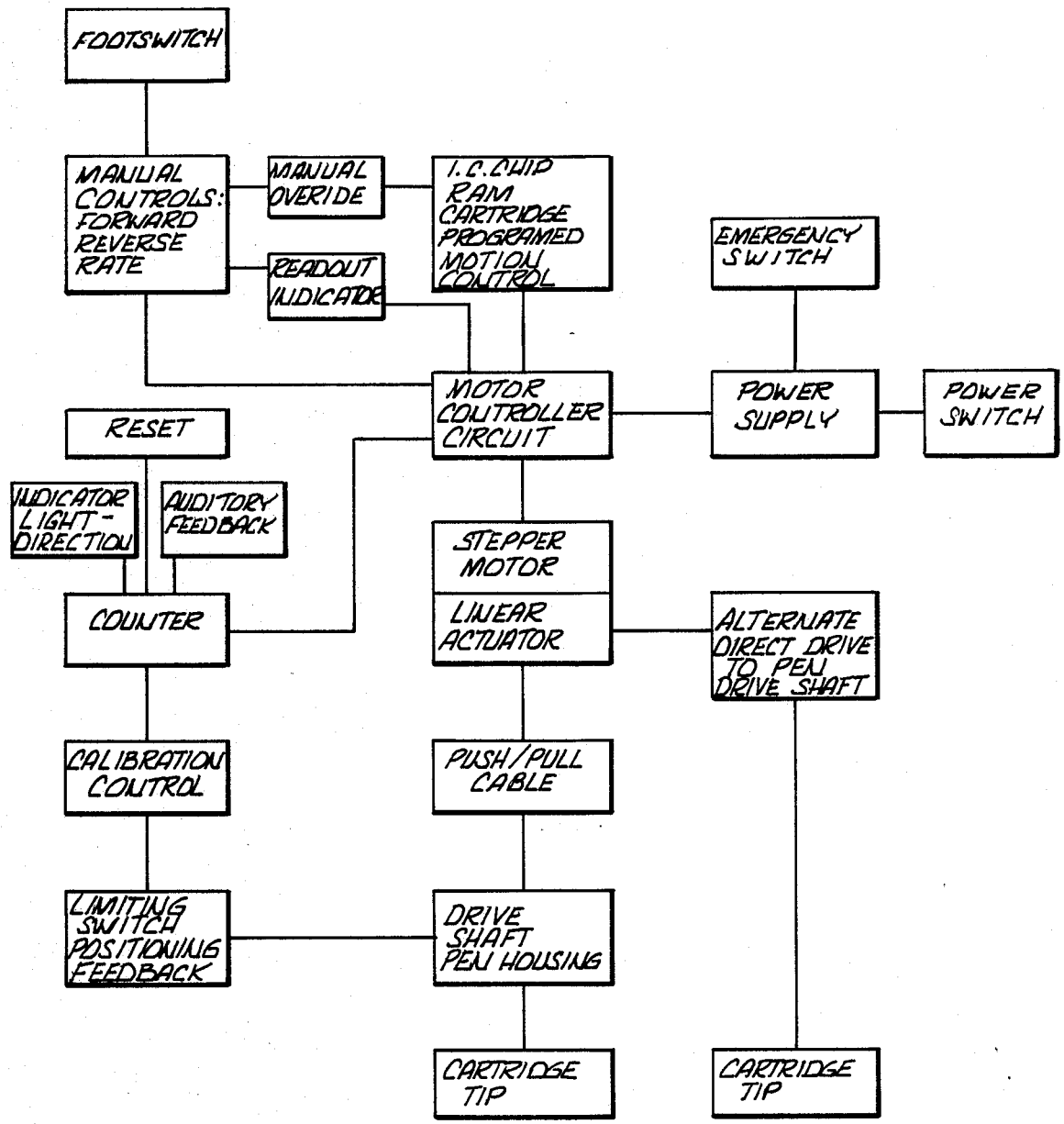
FIG. 8 is an electrical block diagram illustrating the electronic control components of the control unit of FIG. 1.

Turning now to the drawings and first to FIG. 1, the overall lens insertion system includes a control unit 10, hand held instrument or pen 11 and insertion cartridge 12. As will be explained later, the insertion cartridge 12 is a disposable unit which holds a lens in a curled up manner such that the lens can be moved out of the tip 13 of the cartridge 12 under control of the control unit 10.

The description herein will be with reference to insertion of artificial intra-ocular lenses; however, it is to be understood that the concepts of the present invention are applicable to insertion of other forms of artificial lenses into the eye such as in refractive surgery in the cornea. In this latter regard, a relatively thin lens can be inserted through use of the apparatus and methods of the present invention in a "pita pocket" formed in the stroma layer of the cornea by suitable mechanical means. In this case, the insertion tip is approximately one-half the diameter of that shown and described herein. Accordingly, the concepts of the present invention are not to be limited to use and insertion of any particular form of lens in the eye.

The control unit 10 includes a linear actuator or stepper motor (shown in greater detail in FIG. 2 and to be discussed subsequently) which, via a suitable flexible cable assembly 14, gently pushes a delivery envelope and the intraocular lens out of the tip 13 at a controlled rate, such as in one thousandth inch increments and at selectable speeds.

Figure 9:
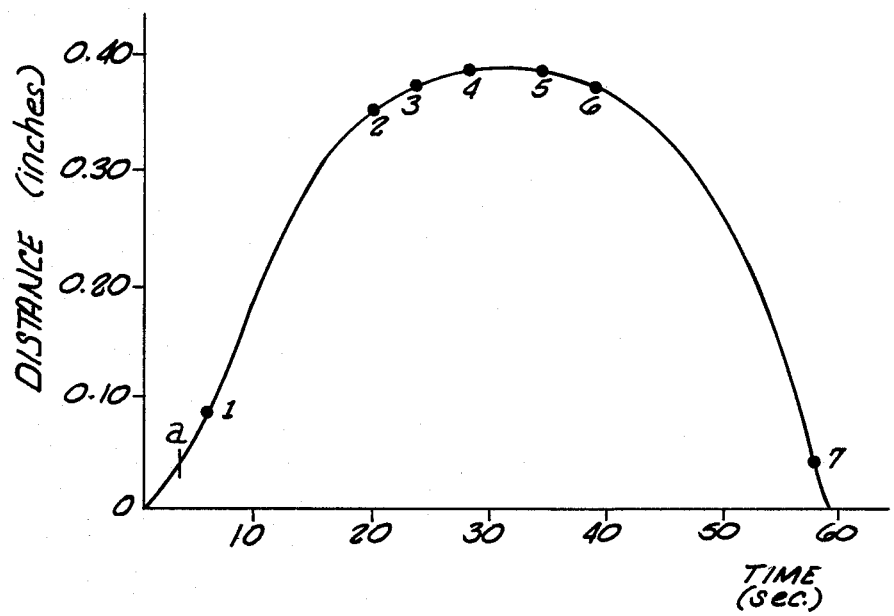
FIG. 9 is a curve illustrating a preferred form of advancement or movement rate of the lens delivery envelope out of and back into the sheath during injection of the lens into the eye under control of the control unit, FIGS. 10a and 10b respectively illustrate the forming of a pocket in the stroma layer of the cornea by mechanical means and the insertion of a lens into the cornea in the pocket thus formed.

The control unit 10 includes a housing 16 on which is provided visual display 17 for indicating the distance travelled by the lens in one thousandth inch increments during the insertion procedure. Also provided is a power on/off switch 18, a speed control potentiometer 19, a forward/reverse direction switch 20, a reset button 21, and automatic control buttons 22a and 22b. A foot switch 25 is connected to the control unit to allow the physician to control the advancement of the intraocular lens. The speed control potentiometer controls the speed of advancement when the foot pedal 25 is depressed. The direction switch 20 selects the direction of advancement or retraction of the driving cable which pushes and pulls the delivery envelope during injection of the intra-ocular lens into the eye as will be explained in greater detail subsequently. The reset button 21 allows the display 17 to be reset to zero. The automatic control buttons 22a-22b allow an internally programmed rate of advancement to be selected (such as is illustrated by the curve of FIG. 9 and which will be discussed later).

FIG. 2 illustrates the stepper motor linear actuator system disposed within the control unit 10 and which is connected to the flexible cable assembly 14. This unit includes a conventional stepper motor linear actuator 30 which drives a shaft 31 linearly (to the right and to the left as viewed in FIG. 2) to drive a cable 32 (note FIGS. 1 and 3) of the flexible push/pull cable assembly 14 through the outer sheath or conduit 33 thereof. The shaft 31 is connected to the cable via a collar 35 and the cable extends through a mounting assembly 36. The actuator 30 and assembly 36 are mounted on a suitable bracket 37 attached through a base 38 to the interior of the housing 16. A stabilizing block 40 is attached to the shaft 31 and rides on bracket 37 to help stabilize the linear movement of the shaft 31.

The foregoing generally describes the overall operation of the control unit, pen and lens injector cartridge. The discussion now will proceed to the details of the injection cartridge 12 and the pen assembly 11 particularly with reference to FIGS. 3 through 7.

Considering FIGS. 3 through 5, and particularly FIGS. 5a–5c, the insertion cartridge 12 comprises the three major components mentioned earlier; namely, a delivery envelope 50 (note FIG. 5a), constricting sheath 51, and slotted reentry barrier 52 (note also, e.g., FIG. 7a for a more detailed cross-sectional view of these components). The proximal end 53 of the delivery envelope 50 is threaded onto a drive shaft 54 of the pen 11, and the proximal end of the sheath 51 is threaded at 55 for attachment to threaded end 56 of the pen 11. The delivery envelope 50 includes a relatively thin (such as 0.035 to 0.0045 inch thick, and 0.158 inch outer diameter) cylindrical distal end 64 terminating in a normally open lens holder section 65. The extreme distal end of cylindrical section 64 is slit at 66 thereby forming sidewalls 67 and 68 which essentially lay open (like a flower petal) to form the lens holder section or "petal" 65. The proximal end 72 of the delivery envelope 50 extends rearwardly of the constricting sheath 51 and has an intermediate key 69 which mates with a slot 70 in the sheath 51 to prevent the envelope 50 from rotating with respect to the sheath 51. This intermediate section of the envelope 50 near the proximal end 72 has an intermediate slot 73 and an interior wall 74 (note FIG. 7a).

The constricting sheath 51 has a relatively thin (0.070 to 0.0045 inch thick, and 0.102 inch outer diameter) cylindrical distal end 76 for confining the delivery envelope 50 in closing it and curling the lens, and which is sufficiently small to be inserted within a small incision in the eye. The sheath 51 and delivery envelope 50 are relatively moveable axially so that the envelope 50 can be withdrawn into and extended out of the tip 76 of the sheath 51. The sheath 51 also includes a body portion 77 terminating in the proximal threaded portion 55 which threads into the threaded distal end 56 of the pen 11. The body 77 includes an elongated slot having sections 79a and 79b with an intermediate wall or stop 80.

The slotted reentry barrier 52 includes a body portion 86 (FIG. 7a) with a distal end 87 having a slot 88 therein for receiving and straddling the rear haptic 59b of the lens 58. The example lens 58 can be a J-style haptic IOL. The barrier 52 also includes an upper finger 89 which extends about half way across the optical portion 58a of the lens 58 to help hold and stabilize the lens. The slot 88 is thick enough for receiving the rear haptic 59b of the lens 58 but is thin enough to prevent the body 59c of the lens 58 from lodging in the slot. The rear portion of the barrier 52 includes a longitudinal arm 90 which has a proximal end 91 for abutting the wall 74 of the envelope 50 so that forward movement (to the right as seen in FIG. 5a and FIG. 7) of the delivery envelope 50 will push against the end 91 and arm 90 and thereby carry the barrier 52 forward along with the delivery envelope 50. The rear or proximal end 91 of the barrier 52 also includes a resilient arm 94 with an upwardly extending (as seen in FIG. 7) stop tab 95. The stop tab 95 functions to engage the retention wall 8 of the constricting sheath 51 after the delivery envelope 50 is extended out of the sheath 51 in injecting the lens 58 and as the delivery envelope 50 is retracted back into the sheath as will be explained in greater detail subsequently.

Turning now to loading of the lens 58 into the insertion cartridge 12, FIGS. 4a and 4b illustrate a combined loading mechanism and sterile package for the insertion cartridge 12. This package may include a container 100 having a base 101 and a pair of channel shaped sidewalls 102 and 103. A first end 105 of the container 100 has a pin 106 affixed thereto for engaging a hole 107 in the proximal end 72 of the delivery envelope 50. The constricting sleeve 51 can rest in a like configured cavity 108 in the base 101 of the container 100 so as to allow the lens holder 65 of the delivery envelope 50 to lay on the bottom 101. The lens 58 can be laid into the lens holder 65 with the rear haptic 59b slid into the slot 88 (FIG. 7a) in the barrier 52, and a clear plastic lens cover 110 can be snapped over the lens 58 and holder 65 between the side rails 102 and 103 to cover and protect the lens. A clear plastic cover (not shown) can be provided over the entire container 100. The container 100 provides a convenient means for holding, storing and transporting the loaded insertion cartridge 12.

The container 100 also has an actuator slide or clip 112 which abuts or straddles the proximal end of the constricting sheet 51 at or near the threads 55 thereof. The actuator slide 112 can be grasped by hand as shown in FIG. 4b to push the constricting sheath while the pin 106 holds the proximal end of the delivery envelope 50 so as to cause the delivery envelope 50 and the reentry barrier 52 to be retracted into the sheath 51 to a final position as shown in FIG. 5b.

A tab 114 with a resilient finger 115 can be pivoted in the direction shown in FIG. 4b and be held with thumb pressure of the operator to brace the lens in place as the constricting sleeve 51 is moved forward by the actuator 112. The tab 114 can be folded back to the position shown in FIG. 4a for storage, shipment and the like. It will be noted from FIGS. 4b and 5a that the optical section 59c of the lens 58 is located in the holder section 65 essentially even with the extreme distal tip of the delivery envelope 50 and that the forward haptic 59a extends outwardly from the lens holder and the inner or rear haptic 59b (note FIG. 7b) extends into the slot 88 of the reentry barrier 52.

The loading operation in FIG. 4 causes the constricting sheath 51 to be moved forward and conform the delivery envelope 50 to the cylindrical tip 76 of the sheath and thereby curl the lens 58, whereby the envelope 50 is conformed to the internal diameter of the sheath 51.

A flexible tab 71 (Note FIG. 5a) is provided on the proximal end 72 of the envelope 50 which functions as a lock or barrier to keep the proximal end 72 from being pushed too far into the sheath 51 (to the right as seen in FIG. 5a or left in FIG. 4b) so that the stop tab 95 is not pushed into slot 79b during lens loading.

Once the lens is loaded into the lens holder 65 of the delivery envelope 50, and the constricting sleeve 51 is moved by the loader of FIG. 4a–4b such that the components are in the position shown in FIG. 5b, the injection cartridge 12 can be attached to the proximal end of the pen 11 as illustrated in FIG. 5c, and as shown in greater detail in FIGS. 6 and 7. A bore 82 of the pen 11 is of a sufficiently small diameter so that as the injection cartridge is inserted into the distal end of the pen, the narrow wall of the bore 82 pushes down the tab 71 and moves it out of the way as seen in FIGS. 6a and 7a–e to thereby allow the distal end 72 of the envelope to move further into the sheath 51 for ultimate ejection of the lens from the holder as will be explained below.

The cable assembly 14 (note FIG. 3) extends through a retaining cap 42 which is threaded at 43 into the proximal end of the pen or instrument 11. A cable collar 44 retains the cable assembly 14 attached to the instrument 11 and acts as a bushing so that the instrument 11 can be rotated without kinking the cable assembly 14. The cable 32 is connected to the drive shaft 54 which rides within an internal bushing in the instrument 11. The key 69 and slot 70 keep the envelope 50 from rotating with respect to the sheath.

After the injection cartridge 12 is loaded with the lens, and the same attached to the pen 11, insertion of the tip of the constricting sleeve into an incision 120 in the eye can commence. In this procedure, the surgeon already has made a small incision (such as 0.2 inch) 117 in the eye 118 in a conventional manner and has removed the clouded natural lens. The insertion cartridge 12 is inserted into the eye as shown in FIG. 6a and the lens 58 is ejected from the cartridge 12 and injected into the eye in the manner shown in FIGS. 6a through 6e and FIGS. 7a through 7e. All of this occurs under the control of the control unit of FIG. 1, and advancement of the delivery envelope, and consequently the lens, can be controlled via the foot pedal 25, reverse/forward switch 20 and a speed control 19. Preferably, the advancement follows a curve like that shown in FIG. 9 and which is automatically controlled by depressing one of the automatic control buttons 22a or 22b of the control unit 10. Usually the envelope 50 will be advanced slightly, such as to point "a" in the curve of FIG. 9, before insertion of the tip 76 into the incision 117 in the eye 118.

After the tip 76 of the sheath 51 is inserted into the incision 117, the drive shaft is driven forward by the actuator 30 of the control unit 10 and under control of the control unit either automatically or manually via the foot switch 25. The drive shaft 54 pushes the delivery envelope 50 forward to position 1 in the curve of FIG. 9. The drive shaft positions the delivery envelope to position 1 and continues to move or advance the delivery envelope 50 following the curve shown in FIG. 9, and at about point 2 thereof the locking tab 95 of the reentry barrier 52 passes beneath the retention wall 80 of the constricting sheath 51 (note FIGS. 6b–6c and 7b–7c). At point 3 on FIG. 9 the locking tab 90 springs back up into forward slot 79b of sheath 51 since it has passed the wall 80, and this position is shown in FIG. 6c. It will be noted from FIG. 6c and FIG. 7b that the delivery envelope 50 and the reentry barrier 52 move together, and this occurs because the wall 91 of the delivery envelope 50 (note FIG. 7b) pushes the arm 90 at the proximal end 91 of the barrier 52 during ejection of the envelope 50 and lens 58. At point 4 in FIG. 9, the envelope 50 is fully extended and unflowered as more fully shown in FIG. 6c and in FIG. 7c. At point 5 in FIG. 9 the envelope 50 has commenced retraction since now the drive shaft 54 starts pulling or retracting the delivery envelope 50 (note FIG. 6d and 7a). At about point 6 in FIG. 9 the locking tab 95 engages or abuts the forward surface of the wall 80 in the sheath 51, thereby preventing the barrier 52 and the lens 58 from retracting with the envelope 50 which is being retracted by the shaft 54 (FIGS. 6d and 7d). As the drive shaft 54 continues to retract the delivery envelope 50, point 7 on the curve of FIG. 9 is reached at which the envelope 50 has been completely withdrawn into the tip 76 of the sheath 51 as shown in FIGS. 6e and 7e, and the lens 58 is free of support by the envelope. Additionally, the previously "flowered" envelope has been fully retracted so that the tip 76 of the sheath 51 can be removed from the incision 120. Thus insertion cartridge 12 now can be removed from the eye and the lens 58 will remain therein.

As noted above, the control unit 10 can provide the rate of advancement curve of FIG. 9 automatically, with the surgeon starting and stopping the movement (be it either the forward movement up to the peak of the curve of FIG. 9 or the reverse movement thereafter) by depressing the foot switch 25 in FIG. 1. The rate curve of FIG. 9 can be programmed into the control system for this purpose. Alternatively, the surgeon can provide this same, or a different, operation manually by operating the foot switch in conjunction with settings of the forward/reverse switch 20 and the speed control 19. In any event, the tip 12 is inserted in the incision 117 in the eye 118 while the envelope is fully retracted (FIGS. 5b, 6a and 7a) and the lens 58 fully curled within the tip 64 of the envelope and within the tip 7 of the sheath 51. Once the lens is unflowered in the eye as shown in FIGS. 6c and 7c, the doctor causes the delivery envelope 50 to be retracted and the drive shaft 54 retracts thereby pulling or retracting the delivery envelope 50. Note that the constricting sheath tip 76 remains in the incision 117 throughout this procedure (FIGS. 6a–6e and 7a–7e) thereby insulating the incision from the dynamic forces of retracting the envelope. The reentry barrier lock tab 95 prevents the barrier 52 from retracting with the delivery envelope 50. Additionally, the distal end 87 (note FIG. 7b) of the reentry barrier 52, and the slot 88 and the finger 89 thereof, block and stabilize the lens in the envelope holder 65 as the envelope is retracted into the tip 76 of the sheath 51. Once the envelope is fully retracted as shown in FIGS. 6e and 7e, the tip 76 can be withdrawn from the incision 120 without enlarging the incision 117.

Thus, a relatively simple means of curling and confining a lens to the inside of the tip 76 of a constricting sleeve 51 via a flexible envelope 50 is provided so as to allow the lens to be inserted into a relatively small incision, then injected into the eye, and then the tip removed.

FIG. 8 is a block diagram of the overall electrical system for allowing manual and automatic control of advancement of the plunger and consequently advancement of the intra-ocular lens. The drive for the flexible cable 32 of the cable assembly 14 is the stepper motor driven linear actuator 30. Preferably, the shaft of the actuator 30 is directly attached to the cable 32 as earlier shown and discussed in connection with FIG. 2. If desired, a smaller linear actuator may be housed in the instrument 11, similar to an electric eraser, as shown and described in said concurrently filed application Ser. No. 172,374.

As will be readily apparent to those skilled in the art, a fine and highly controlled motion is essential to the safe methodical delivery of the IOL 58. It is desired that the rate of advancement and retraction of the drive shaft vary over the delivery cycle as previously discussed in connection with FIG. 9, and that careful motion control be provided throughout the entire cycle.

The combination of manual controls, programmed controls and foot switch control can provide the physician with accurate control down to 0.0005 inch per second. The direction and rate of the actuator may be controlled with the switch 20 and potentiometer 19 on the console of the control unit 10 discussed earlier.

In operation, the actual triggering of the actuator for movement of the plunger is achieved by depressing the foot switch 5. The system may be arranged so that the foot switch will also control rate like an accelerator pedal, and the surgeon can have the option to determine whether the foot switch includes rate control in addition to its on/off switching functions to advance the plunger. A suitable IC RAM chip 120 for providing programmed motor control (such as is indicated in FIG. 9) is provided in the control system to provide control of a motor control circuit 121 which controls the stepper motor and linear actuator 30. power supply 122 is provided which is turned on and off with the on/off power switch 18 on the front panel of the control unit 10, and an emergency on/off switch 123 can be provided if desired. The foot switch 25, speed potentiometer 19 and forward/reverse switch 20 are connected, along with a manual override/automatic switch 22 and readout indicator 17, with the RAM chip 120 and the motor control circuit 121 to control the direction and speed of the actuator 30, as well as enable control of the same manually or automatically as previously discussed. In an automatic mode as selected by the switch 22, the foot switch 25 can operate merely to turn on and off the automatic rate control of the nature shown in FIG. 9. Additionally, a program delivery sequence of the type shown in FIG. 9 can be provided for each different type intra-ocular lens. Throughout the delivery of the lens, the digital display 17 can indicate the distance travelled, and direction and rate indicators can be provided if desired, such as a direction indicator 130. Auditory feedback can be provided as indicated at 131 to signal or alert the doctor at key points of the delivery cycle. A counter 132 is provided to keep track of the movement and direction. Additionally, and if desired, suitable feedback can be provided from the instrument 11 by positioning feedback circuit 134 and through calibration control 135 in a conventional closed loop servo control fashion.

Figure 10A:
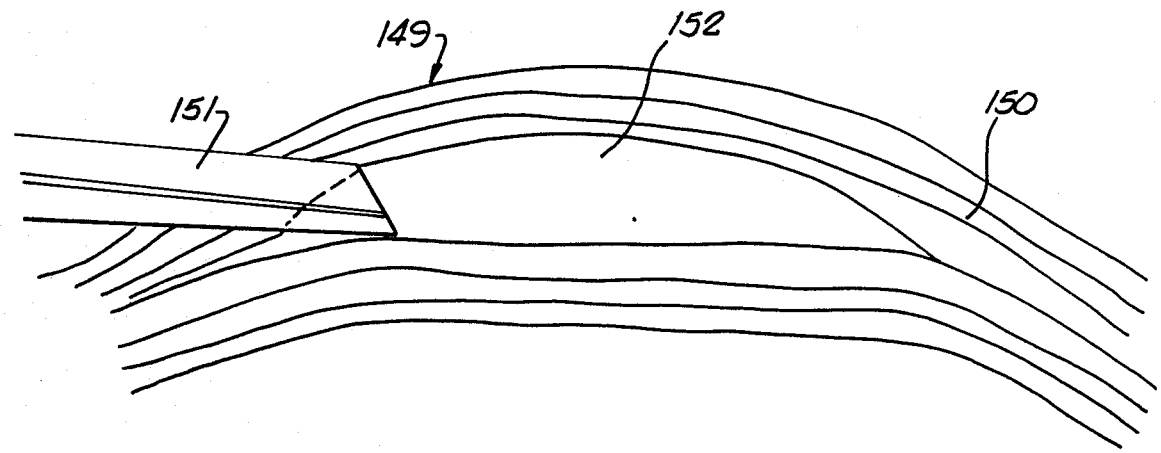
Figure 10B:
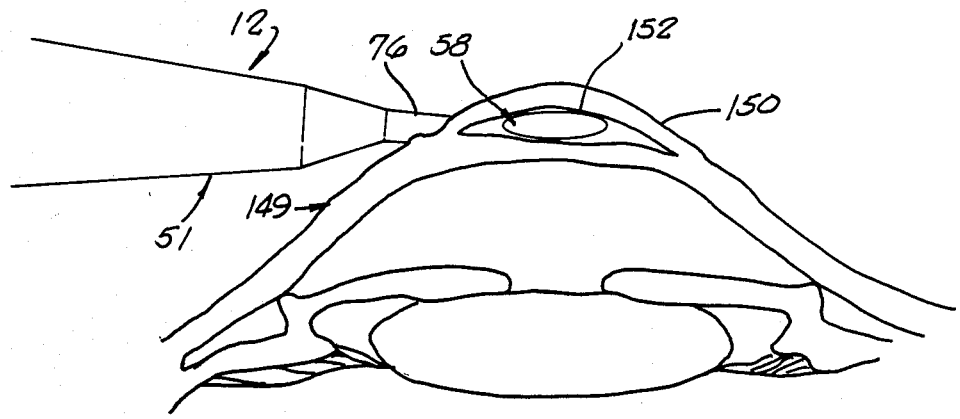

FIG. 10a illustrates the manner in which a pocket or "pita pocket" can be formed in the stroma layer 150 of the cornea of the eye 149 by suitable mechanical means, such as by pneumatic or hydraulic pressure or by a blade cut as illustrated by instrument 151 forming a pocket 152. FIG. 10b illustrates the insertion of an artificial lens 58 into the thus-formed pocket 52 in the stroma layer 150 via the insertion cartridge 12. This is an example of how the concepts of the present invention are applicable to insertion of an artificial lens into the eye in refractive surgery in the cornea.

Figure 11A:
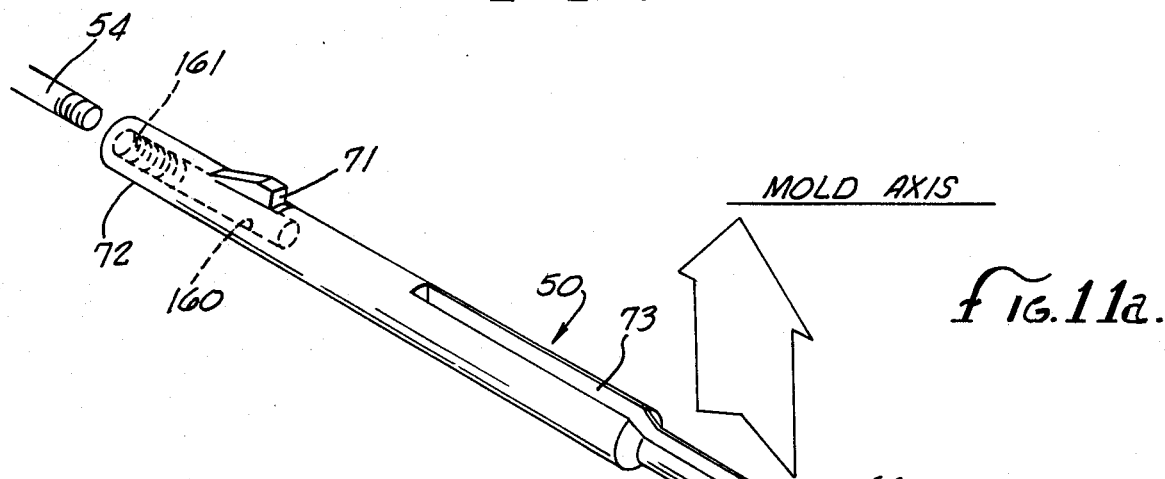
FIGS. 11a and 11b are respectively a perspective view and a cross-sectional view illustrating the manner in which the delivery envelope is molded.
Figure 11B:
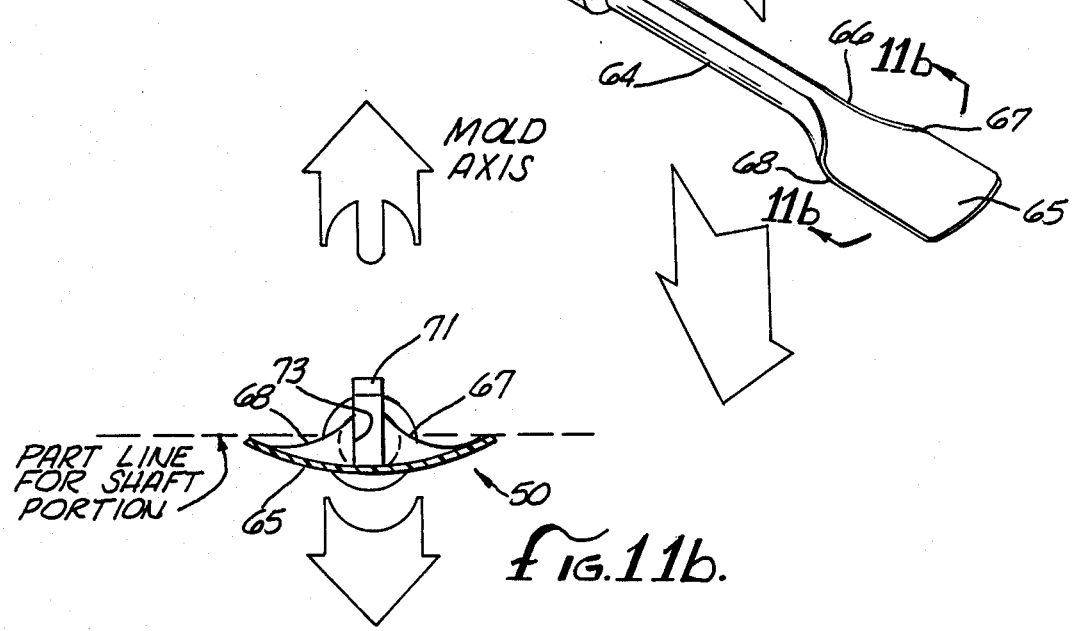

The envelope 50 may be injection molded using conventional molding techniques. The envelope preferably is molded from clear polyethylene. The envelope is molded with the petal 65 in the open position as shown in FIGS. 11a-11b. The slot 73 which terminates in the distal slot or slit 66 also is molded during the molding process, as is a core 160 and internal threads 161. The latter are formed by a threaded pin 162. The core 160 allows the tab 71 to be depressed into the hollow area formed by the core.

The stepper motor 30 may be an Airpax model K92211-P2 or equivalent twelve volt unit. It may be driven directly from a Signetics SAA1024 controller chip. The motor speed may be controlled through a variable frequency oscillator and scaler which can be activated by the foot control switch. Preferably, the stepper position is displayed in 0.001 inch increments on a three digit seven segment display of conventional design. The position indicated is relative since the display may be reset as previously explained to zero at any time and then the display value will represent positive or negative steps from the last reset position. The normal operation allows the physician to select the direction, reset the display to zero and then increment the position in 0.001 inch increments as long as the foot switch is depressed. A typical full range is 0.875 inch equaling a count of 875 on the display. The potentiometer control allows linear speed control of advancement, and preferably provides operation in a range from about five steps per second to one hundred fifteen steps per second which translates approximately to 0.75 inch in 150 seconds minimum speed or 0.75 inch in 6.5 seconds maximum speed.

While embodiments of the present invention have been shown and described, various modifications may be made without departing from the spirit and scope of the present invention, and all such modifications and equivalents are intended to be covered.

What is claimed is:

1. Apparatus for inserting a flexible lens into an eye through an incision in the eye comprising
    lens holder means for receiving and holding a flexible lens, said holder means including a holder having substantially a flower petal shape when the holder is in an opened condition thereof in which a lens can be placed when the lens is in a normal flat state, the holder being formed of a molded thin tubular section of plastic material having an open tip area with outwardly extending sides thereby forming a holder for the lens, said holder sides being curlable to essentially the form of a closed hollow cylinder with a cylindrical inner surface when in a closed condition to curl a lens therein into a generally confined tubular shape,
    sleeve means having a thin cylindrical end for slidably engaging said lens holder means for moving the sides of the holder means together for curling said lens,
    barrier means within said holder means and said sleeve means and movable with respect to said sleeve means and said holder means, said barrier means having a distal end for normally engaging the lens when the lens is in the holder of the holder means, and
    control means for moving said lens holder means and barrier means with respect to and out of said sleeve means, and for retracting said holder means into said sleeve means, for injecting the lens into an eye.

2. Apparatus as in claim 1 wherein
    said sleeve means and barrier means have cooperative locking means for allowing said barrier means to move in one direction with respect to said sleeve means during movement of said holder means out of said sleeve means, and for preventing movement of said barrier means with respect to said sleeve means when said holder means is moved in a second retracted direction into said sleeve means.

3. Apparatus as in claim 2 wherein said cooperative locking means comprises a locking tab disposed on said barrier means for engaging a wall in a slot of said sleeve means.

4. Apparatus a in claim 1 wherein
the distal end of said barrier means includes a thin slot for receiving a haptic of the lens, and the distal end of the barrier means includes a finger for stabilizing, in combination with said slot and said lens holder means, a lens during insertion of the lens into an eye.

5. Apparatus as in claim 1 wherein
said barrier means is disposed within said lens holder means for slidable movement with respect thereto, and said lens holder means includes a wall for engaging an end of the barrier means to cause said barrier means to move with said lens holder means as said lens holder means is moved from said sleeve means, and said sleeve means and said barrier means include cooperative locking means to lock said barrier means with respect to said sleeve means for enabling said holder means to be retracted into said sleeve means without retraction therewith of said barrier.

6. Apparatus as in claim 1 including
instrument means constructed to be hand held by a surgeon, said instrument means having a first end for receiving drive shaft means to be coupled with an end of said lens holder means and having a second end for connection with said sleeve means, and control means including linear actuator means coupled with said drive shaft means for enabling controllable advancement and retraction of said lens holder means in small increments with respect to said sleeve means.

7. Apparatus as in claim 1 wherein the cylindrical end of said sleeve means has a diameter of less than approximately two tenths inch.

* * * * *